US010932800B2

(12) United States Patent
Porter, IV

(10) Patent No.: US 10,932,800 B2
(45) Date of Patent: Mar. 2, 2021

(54) METHODS AND APPARATUS FOR RETROGRADE PERCUTANEOUS ENDOVASCULAR FILTER AND EMBOLECTOMY/THROMBECTOMY DEVICE

(71) Applicant: High Desert Radiology, P.C., Kingman, AZ (US)

(72) Inventor: Christopher A. Porter, IV, Kingman, AZ (US)

(73) Assignee: High Desert Radiology, P.C., Kingman, AZ (US)

(*) Notice: Subject to any disclaimer, the term of this patent is extended or adjusted under 35 U.S.C. 154(b) by 249 days.

(21) Appl. No.: 15/875,822

(22) Filed: Jan. 19, 2018

(65) Prior Publication Data

US 2019/0223892 A1 Jul. 25, 2019

(51) Int. Cl.
*A61B 17/221* (2006.01)
*A61F 2/01* (2006.01)

(52) U.S. Cl.
CPC ............ *A61B 17/221* (2013.01); *A61F 2/013* (2013.01); *A61F 2002/016* (2013.01)

(58) Field of Classification Search
CPC ............ A61B 17/221; A61B 17/12172; A61B 2017/2215; A61B 2017/2212; A61F 2/013; A61F 2002/018; A61F 2002/011; A61F 2230/0006; A61F 2230/0067; A61F 2230/008; A61F 2230/005; A61F 2230/0071; A61M 2025/09183; A61M 25/0133; A61M 25/09
See application file for complete search history.

(56) References Cited

U.S. PATENT DOCUMENTS

| | | |
|---|---|---|
| 4,611,594 A | 9/1986 | Grayhack et al. |
| 6,468,291 B2 | 10/2002 | Bates et al. |
| 6,926,725 B2 | 8/2005 | Cooke et al. |
| 7,371,248 B2 | 5/2008 | Dapolito et al. |
| 7,618,434 B2 | 11/2009 | Santra et al. |
| 7,771,452 B2 | 8/2010 | Pal et al. |
| 8,801,750 B2 | 8/2014 | Cully et al. |
| 8,845,677 B2 | 9/2014 | Pal |
| 9,005,242 B2 | 4/2015 | Cahill |
| 9,427,252 B2 | 8/2016 | Sos |
| 2003/0153943 A1 | 8/2003 | Michael et al. |
| 2003/0187475 A1 | 10/2003 | Tsugita et al. |

(Continued)

FOREIGN PATENT DOCUMENTS

WO 2009/094522 A1 7/2009

*Primary Examiner* — Mohamed G Gabr
(74) *Attorney, Agent, or Firm* — The Noblitt Group, PLLC

(57) ABSTRACT

Methods and apparatus for a percutaneous retrograde endovascular filter and embolectomy/thrombectomy device (RET-D) according to various aspects of the present technology include a constraining sleeve housing a deployable filter and a set of closure struts positioned at the end of a flexible tube. The RET-D is deployed into a target vessel in retrograde fashion through a conventional hemostasis sheath such that the open end of the filter engages the antegrade flow of blood. The closure struts are configured to prevent loss of filtered debris when the filter is closed according to where the closure struts are positioned relative to an end of the constraining sleeve.

16 Claims, 7 Drawing Sheets

(56) References Cited

U.S. PATENT DOCUMENTS

| | | | |
|---|---|---|---|
| 2006/0047286 A1* | 3/2006 | West | A61B 17/221 606/114 |
| 2008/0269774 A1* | 10/2008 | Garcia | A61B 17/221 606/127 |
| 2009/0222035 A1 | 9/2009 | Schneiderman | |
| 2011/0130657 A1* | 6/2011 | Chomas | A61B 17/12172 600/433 |
| 2013/0138138 A1 | 5/2013 | Clark et al. | |
| 2015/0265299 A1 | 9/2015 | Cooper et al. | |

* cited by examiner

METHODS AND APPARATUS FOR RETROGRADE PERCUTANEOUS ENDOVASCULAR FILTER AND EMBOLECTOMY/THROMBECTOMY DEVICE

BACKGROUND OF THE TECHNOLOGY

Various devices and methods exist to protect distal vasculature from dislodged thrombus (blood clot) and embolus (organized intravascular body) when proximal vascular interventions/surgeries are being performed. Further, multiple methods of removing a thrombus or embolus exist including open surgical intervention. Distal embolization caused by peripheral arterial disease (PAD) interventions are a significant cause of morbidity following PAD endovascular revascularization. There are various devices and techniques to prevent emboli and blood clots from traveling within the vasculature such as the use of deployable basket filters that are deployed in the antegrade (in the direction of blood flow) approach along a guide wire inserted into a target vessel or lumen. Some of these devices actively attempt to displace and catch thrombus and emboli while others are positioned to catch any masses that are dislodged during a separate arterial intervention procedure. Some of these filter devices are designed to be left in place but may dislodge and be carried downstream where they can form a blockage themselves. Another common trait to each of these efforts is that they are deployed in the same direction as blood flow through the vessel or lumen. This arrangement may reduce the effectiveness because antegrade approaches for device positioning and deployment necessitates crossing the donor site of emboli/thrombus, thereby causing inadvertent distal embolization. For this reason, traditional antegrade mechanisms of embolic protection are often causing the problem they are designed to protect against. Further, traditional deployment system mechanisms are often prone to failure, resulting in additional procedures and open surgery to remove irretrievable or lost filter devices.

SUMMARY OF THE TECHNOLOGY

Methods and apparatus for a percutaneous retrograde endovascular filter and embolectomy/thrombectomy device (RET-D) according to various aspects of the present technology include a constraining sleeve housing a deployable filter and a set of closure struts positioned at the end of a flexible tube. The RET-D is deployed into a target vessel in retrograde fashion through a conventional hemostasis sheath such that the open end of the filter engages the antegrade flow of blood. The closure struts are configured to prevent loss of filtered debris when the filter is closed according to where the closure struts are positioned relative to an end of the constraining sleeve.

BRIEF DESCRIPTION OF THE DRAWINGS

A more complete understanding of the present technology may be derived by referring to the detailed description and claims when considered in connection with the following illustrative figures. In the following figures, like reference numbers refer to similar elements and steps throughout the figures.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of hardware components configured to perform the specified functions and achieve the various results. For example, the present technology may employ various materials, needles, wires, injectable devices, dilators, ports, and the like, which may carry out a variety functions. In addition, the present technology may be practiced in conjunction with any number of applications, and the system described is merely one exemplary application for the technology.

Figure 1A:
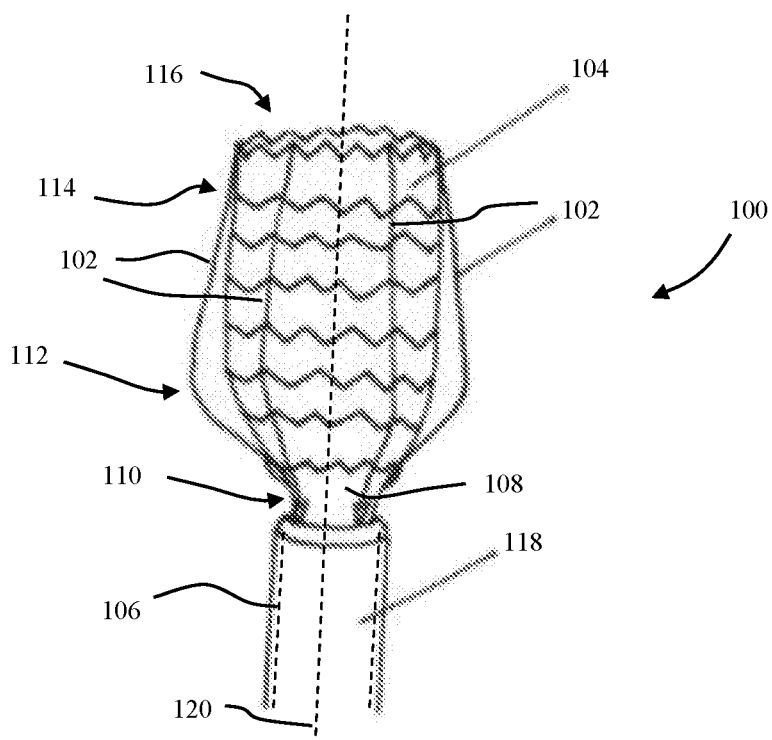
FIG. 1A representatively illustrates a filter device in a semi-open position in accordance with an exemplary embodiment of the present technology.
Figure 1B:
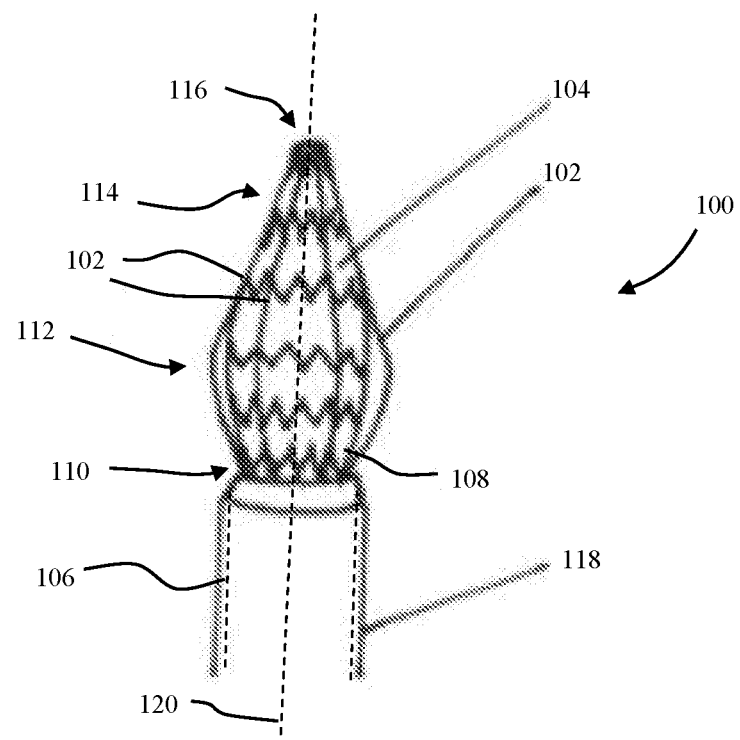
FIG. 1B representatively illustrates the filter device in a closed positioned in accordance with an exemplary embodiment of the present technology.

Referring now to FIGS. 1A and 1B a percutaneous retrograde endovascular filter and embolectomy/thrombectomy device (RET-D) according to various aspects of the present technology may comprise a constraining sleeve 118 housing a filter device 100 in a constrained manner. The filter device 100 may be suitably configured to slide within the constraining sleeve 118 such that the filter device 100 can be extended out the end of the constraining sleeve 118. The filter device 100 may comprise a flexible tube 106 having a filter 104 at a first end and a set of deployable struts 102 arranged peripherally around the filter 104. The filter device 100 may comprise any suitable filtering system or apparatus to capture a thrombus (blood clot) or embolus (unattached mass) in a target vessel such as an artery or vein.

Figure 3:
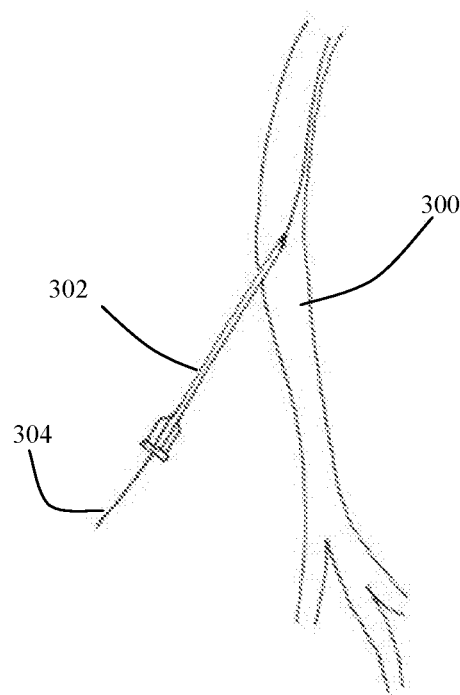
FIG. 3 representatively illustrates percutaneous access into a target vessel in retrograde fashion in accordance with an exemplary embodiment of the present technology.
Figure 4:
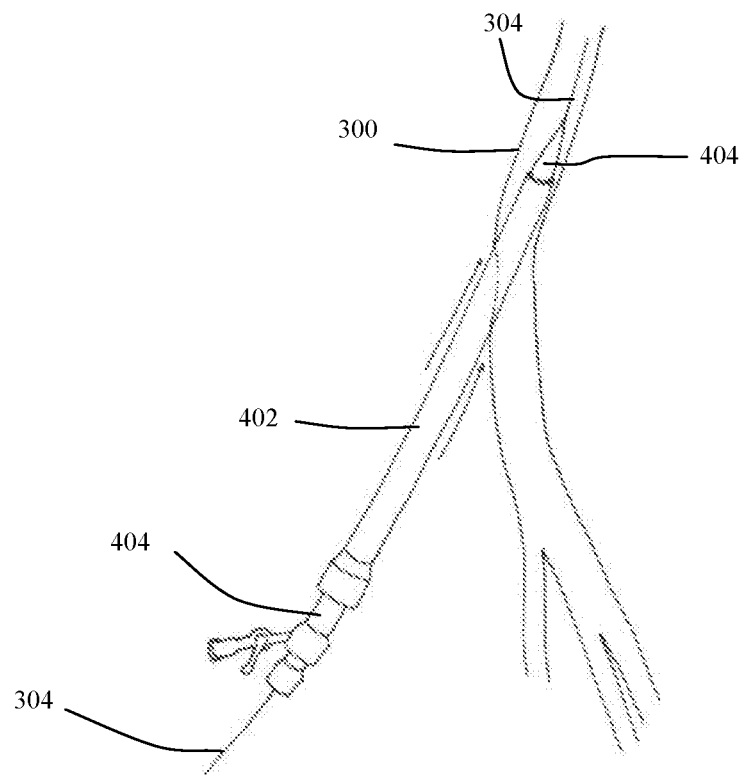
FIG. 4 representatively illustrates insertion of a hemostasis sheath and dilator in accordance with an exemplary embodiment of the present technology.
Figure 5:
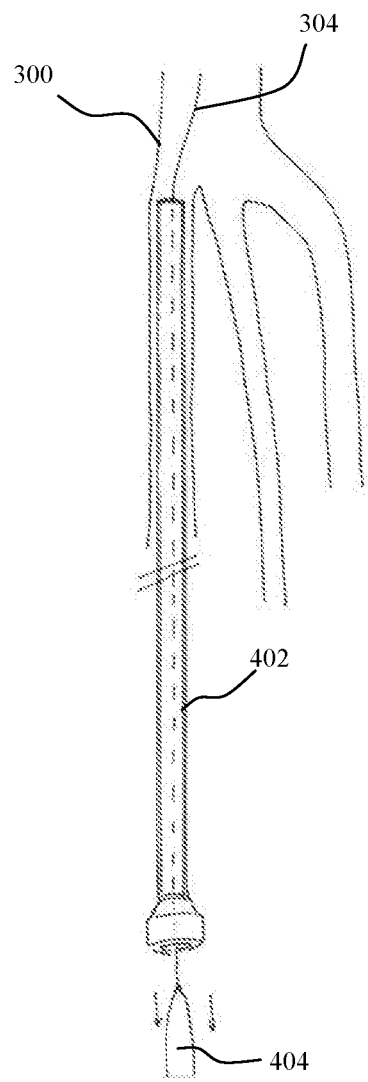
FIG. 5 representatively illustrates removal of the dilator in accordance with an exemplary embodiment of the present technology.

Referring to FIGS. 3 and 4, the filter device 100 may be deployed into a target vessel 300 by any suitable method or process. In an exemplary embodiment, the filter device 100 is installed percutaneously (through the skin) into the target vessel 300 in retrograde fashion (opposite blood flow) through a standard hemostasis sheath 402. A series of tear away sheaths and other commonly known percutaneous access devices such as needles, vascular dilators, and guide wires may be utilized to position and deploy the filter device 100.

Filter Device

Figure 8:
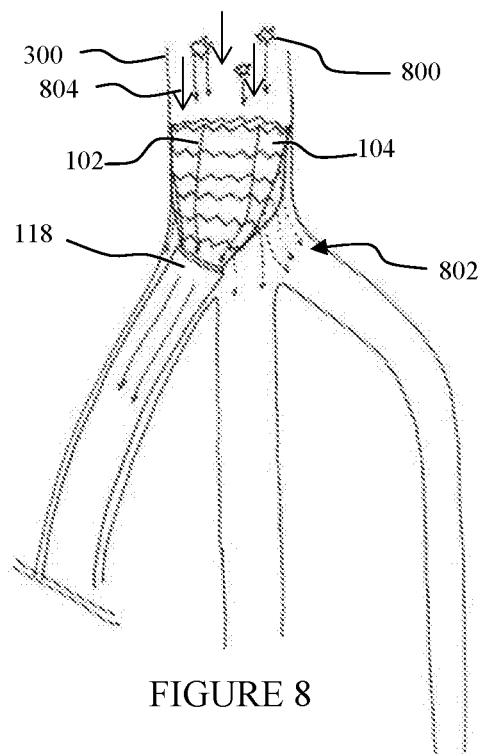
FIG. 8 representatively illustrates the filter device in a deployed position in accordance with an exemplary embodiment of the present technology.

Referring now to FIGS. 1A, 1B, and 8, once the filter device 100 is positioned in the target vessel 300, the filter 104 filters an oncoming blood supply. The filter 104 may comprise any suitable material or combinations of materials suitable for use inside the human body such as natural or synthetic polymers or metal alloys that are suitably configured to allow blood flow 804 to pass while filtering out particles greater than a desired size. For example, in one embodiment, the filter 104 may comprise a material such as nitinol mesh configured to filter out particles greater than five to ten percent of diameter of distal vasculature. In an alternative embodiment, the filter 104 may comprise a polymer such as a porous polytetrafluoroethylene (PTFE) matrix configured to filter out particles greater than five to ten percent of the diameter of distal vasculature. In an alternative embodiment, the filter 104 may comprise a synthetic or metallic mesh configured to filter out particles greater than the diameter of five to ten percent of distal vasculature.

Figure 6:
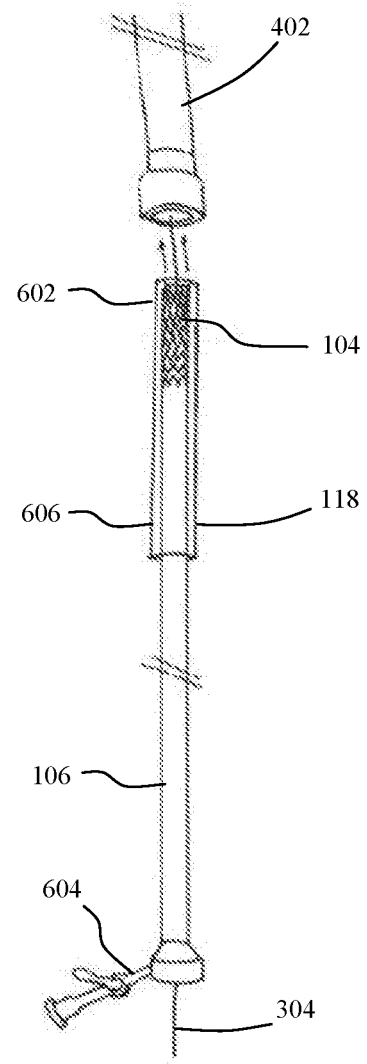
FIG. 6 representatively illustrates insertion of the RET-D into the hemostasis sheath using a sliding constraining sleeve in accordance with an exemplary embodiment of the present technology.

The filter 104 may comprise a flexible body having a base 108 disposed at the first end of the flexible tube 106 and an open end 116 opposite the base 108. The filter 104 may be configured to move from an initially constrained state prior to deployment (FIG. 6), to a fully open state during deployment (FIG. 8), and finally to a closed state after a filtering procedure is completed (FIG. 9).

In the deployed position, the open end 116 of the filter 104 may expand outwardly from a central axis 120 of the filter device 100 to the inner wall of the target vessel 300 to direct the oncoming blood flow 804 into an inner surface of the filter 104. Filtered blood 802 may pass through the filter 104 and any thrombus or emboli 800 contained in the blood flow 804 may be captured by the filter 104 and directed towards the base 108. The base 108 is open to the flexible tube 106 and may allow for the collected thrombus or emboli 800 to be aspirated through the flexible tube 106.

Figure 9:
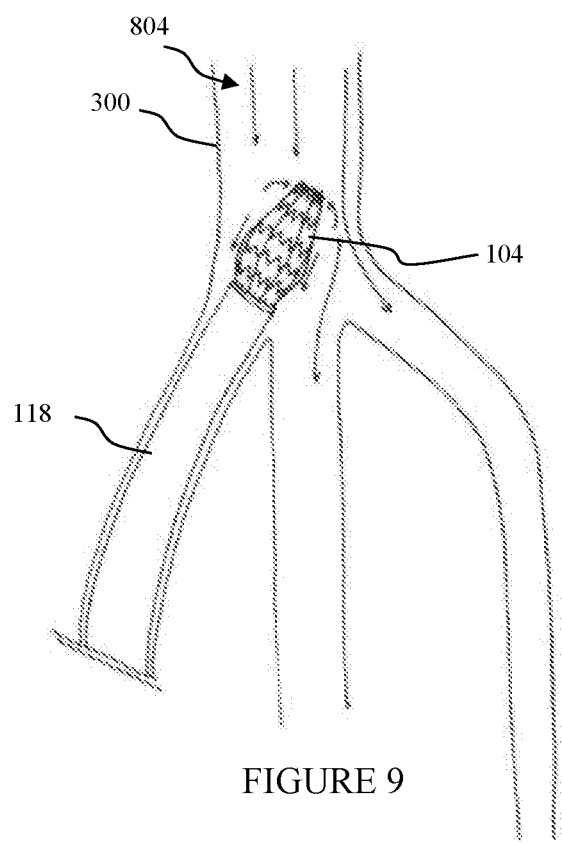
FIG. 9 representatively illustrates the filter device in a partially withdrawn position in accordance with an exemplary embodiment of the present technology.
Figure 10:
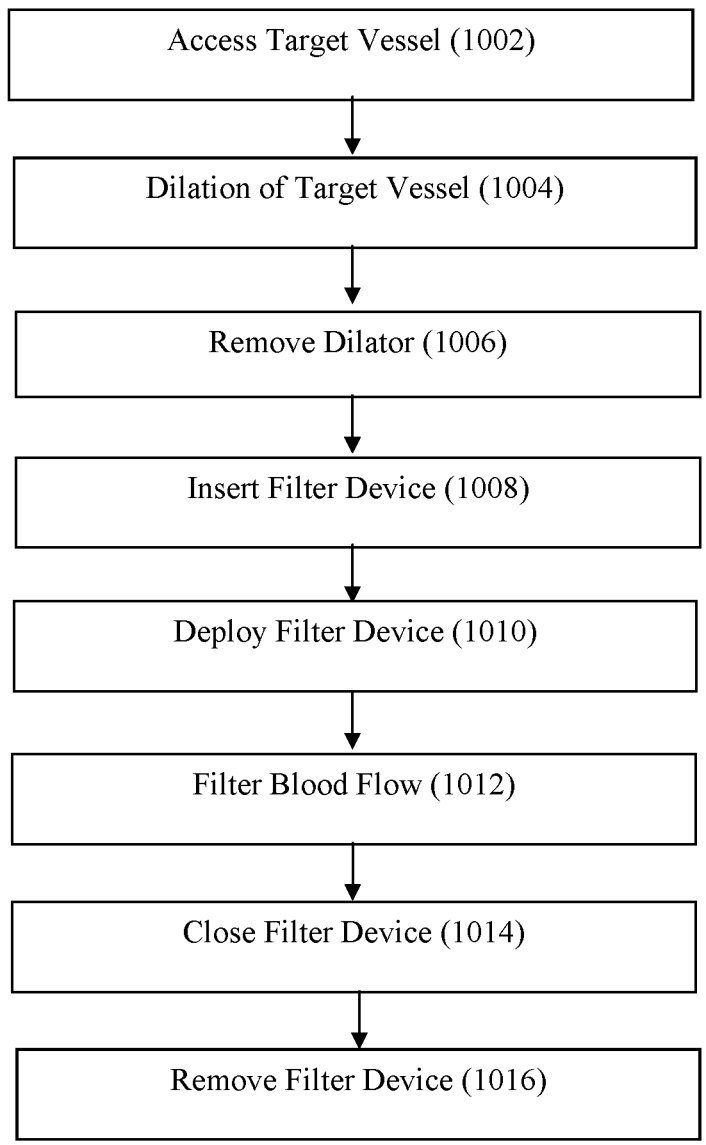
FIG. 10 is a flowchart of the process of using the filter device in accordance with an exemplary embodiment of the present technology.

Referring now to FIGS. 1B and 9, the filter 104 may be closed upon the completion of the filtering procedure to prevent any collected material that hasn't been aspirated from moving out of the filter 104 and back into the target vessel 300. For example, the open end 116 may be moved away from the inner wall of the target vessel 300 and back towards the central axis 120 in a manner that closes the open end 116 while leaving a space between the open end 116 and the base 108 partially expanded to form a tulip shape. Collected material may be retained in the tulip shaped area while the closed open end 116 prevents the collected material from escaping the filter device 100 during removal.

Flexible Tube

Referring to FIGS. 1A, 1B, 6, and 7, the flexible tube 106 slides relative to the constraining sleeve 118 to position and retrieve the filter 104. The flexible tube 106 may comprise any suitable system or device deploying and withdrawing the filter 104 from the constraining sleeve 118. For example, the flexible tube 106 may be configured similarly to the hemostasis sheath 402 and may be made of similar materials.

The first end of the flexible tube 106 may comprise the filter 104 and the set of deployable struts 102. A second end of the flexible tube may comprise an aspiration port 604 used to remove collected thrombus or emboli 800 from the filter device 100.

Struts

Referring now to FIGS. 1A, 1B, 2A, and 2B, the set of deployable struts 102 act to open and close the open end 114 of the filter 104. The set of deployable struts 102 may comprise any suitable device for assisting with the opening and closing of the filter 104 and may provide some support to the filter 104 during the filtering procedure. In one embodiment, the set of deployable struts 102 are arranged peripherally around the filter 104 and may be positioned between the filter 104 and an inner wall of the constraining sleeve 118 prior to deployment.

The set of deployable struts 102 may comprise any suitable number of individual struts 102. The number of struts 102 may be selected according to any suitable criteria such as a diameter of the target vessel 300 or an expected blood pressure at the deployment location. For example, in one embodiment, the set of deployable struts 102 may comprise between three and seven individual struts 102 equally spaced around the periphery of the filter 104.

The set of deployable struts 102 may comprise any suitable material such as a stainless steel wire formed in a predetermined shape. For example, and referring now to FIGS. 1A and 2A, in one embodiment, each strut 102 from the set of deployable struts 102 may comprise a memory wire made of nitinol. Each strut 102 may comprise a lower section 110 that extends outwardly away from central axis 120 and the base 108 of the filter 104 to a mid-portion 112. An upper section 114 of each strut 102 may extend inwardly from the mid-portion 112 towards the central axis 120 to an end 202. The end 202 of each strut 102 may be coupled or otherwise connected to a section of the open end 116 of the filter 104.

Accordingly, the set of deployable struts 102 may be configured to open and close the filter 104 according to their position relative to the constraining sleeve 118. For example, referring to FIGS. 1A, 2A, and 8, when the filter device 100 is extended out of the constraining sleeve 118 to the deployed position, the set of deployable struts 102 expand outwardly away from the central axis 120 to a diameter that is greater than that of the constraining sleeve 118. As the ends 202 of each strut 102 expand outward and away from each other, they cause the open end 116 of the filter 104 to also extend outwardly away from the central axis 120 thereby opening the filter 104 and exposing an inner surface of the filter 104 to the oncoming blood flow 804. The lower section 110 and mid-portion 112 may provide support to the filter 104 to prevent the filter from collapsing or being carried away under the pressure of the passing blood flow 804.

Figure 2A:
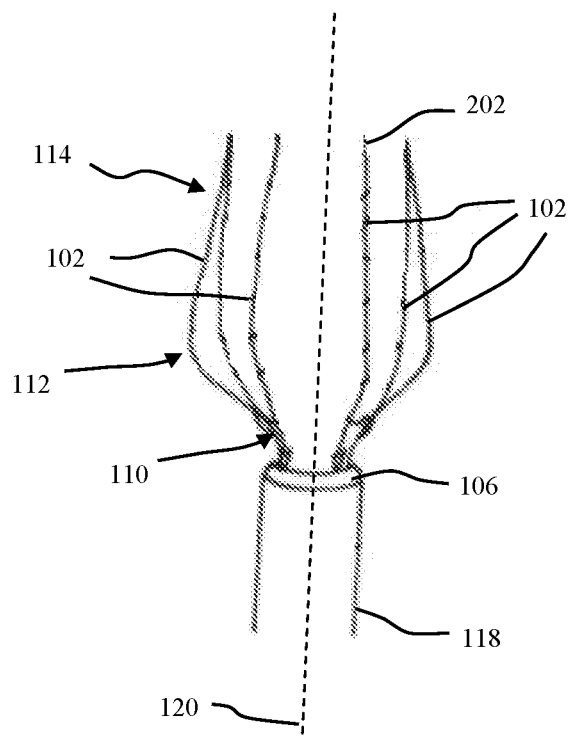
FIG. 2A representatively illustrates a set of struts in the semi-open position in accordance with an exemplary embodiment of the present technology.
Figure 2B:
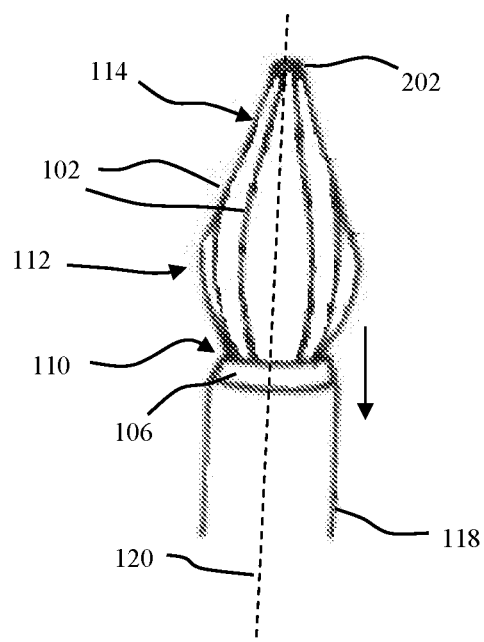
FIG. 2B representatively illustrates the set of struts in the closed position in accordance with an exemplary embodiment of the present technology.

Referring to now FIGS. 1B, 2B, and 9, when the filter device 100 is partially withdrawn back into the constraining sleeve 118, a section of each strut 102 between the lower section 110 and the mid-portion 112 comes into contact with the end of the constraining sleeve 118. As the filter device 110 is drawn into the constraining sleeve 118, forces applied to the struts cause the upper section 114 to move back towards the central axis 120 until the ends 202 of each strut 102 meet closing the filter 104. Once the open end 116 of the filter 104 is closed, the mid-portion of each strut 102 is contracted to a second diameter approximate that of the constraining sleeve 118.

Constraining Sleeve

The constraining sleeve 118 houses a portion of the filter device 100 in a constrained state until deployment. The constraining sleeve 118 may comprise any suitable device or system configured to be partially inserted into the hemostasis sheath 402 and allow the filter device 100 to slide along its interior to facilitate deployment and withdrawal of the filter device 100. The constraining sleeve 118 may comprise an insertion end 602 enclosing the filter 104 and the deployable struts 102 and a second end 606 with a cuff lumen extending between the insertion 602 and the second end 606. The flexible tube 106 of the filter device 100 may extend out of the second end 606 of the constraining sleeve 118.

In operation and referring now to FIGS. 3-10, a percutaneous thrombectomy procedure may be performed by identifying a target vessel 300 and inserting an access needle 302 into an interior of the target vessel 300. A guide wire 704 may be inserted through the access needle 302 and into the target vessel 300 (FIG. 3) (1002). The access needle 302 may then be removed and dilation of the target vessel 300 may be performed by sliding a hemostasis sheath 402 over the guide wire 304 and positioning a dilator 404 over the guide wire 704 and then into the lumen of the hemostasis sheath 402 through the insertion end and subsequently into the target vessel 300 (FIG. 4) (1004).

The dilator 404 may then be removed from the target vessel 300 by sliding it outwardly away from hemostasis sheath 402 (FIG. 5) leaving the guide wire 304 and hemostasis sheath 402 in place (1006).

Figure 7:
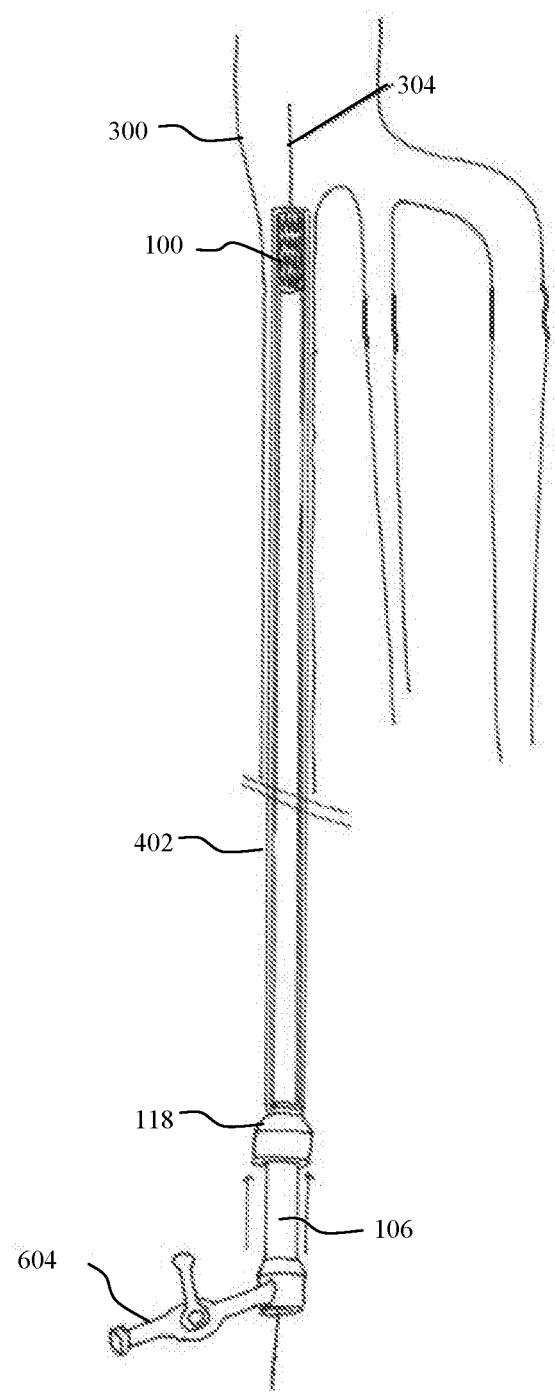
FIG. 7 representatively illustrates retrograde positioning of the RET-D, constrained within the hemostasis sheath in the target vessel in accordance with an exemplary embodiment of the present technology.

The constraining sleeve 118 containing the filter device 100 is then positioned over the guide wire 304 and slid into the hemostasis sheath 402 (FIG. 6) (1008). The constraining sleeve 118 extends partially into the hemostasis sheath 402 (FIG. 7). The flexible tube 106 is then used to deploy the filter 104 by sliding the filter 104 and deployable struts 102 out from the end of the constraining sleeve 118 and into the target vessel 300 (FIG. 8) (1010).

Upon completion of the filtering procedure, the filter 104 and the deployable struts 102 may be partially withdrawn back into the constraining sleeve 118 such that the lower end of the deployable struts 102 abut the insertion end of the constraining sleeve 118 causing the filter 104 to close (FIG. 9) (1014) in a manner that prevents spillage of filtered embolic debris. The filter device 100 may then be withdrawn from the target vessel 300 through the hemostasis sheath 402 (1016).

These and other embodiments for methods of filtering a material flowing through a lumen may incorporate concepts, embodiments, and configurations as described above. The particular implementations shown and described are illustrative of the technology and its best mode and are not intended to otherwise limit the scope of the present technology in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

The technology has been described with reference to specific exemplary embodiments. Various modifications and changes, however, may be made without departing from the scope of the present technology. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present technology and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to an exemplary embodiment. However, changes and modifications may be made to the exemplary embodiment without departing from the scope of the present technology. These and other changes or modifications are intended to be included within the scope of the present technology, as expressed in the following claims.

The invention claimed is:

1. A system for percutaneous retrograde endovascular filtering and embolectomy/thrombectomy, comprising:
   a constraining sleeve, comprising:
      an insertion end;
      a second end; and
      a sleeve lumen extending between the insertion end and the second end;
   a filter device disposed and configured to slide within the sleeve lumen to move between a deployed position out of the insertion end and a partially withdrawn position abutting the insertion end, wherein the filter device comprises:
      a flexible tube;
      a filter comprising:
         a base disposed at a first end of the flexible tube; and
         an open end opposite the base, wherein the base and the open end are constrained within the insertion end prior to deployment; and a set of deployable independent struts positioned around an outer periphery of the filter, wherein:
a first end of each strut:
is coupled to the open end of the filter;
expands outwardly to open the filter when the filter device is in the deployed position; and
contracts to close the filter when the filter device is in the partially withdrawn position;
a second end of each strut is coupled to the flexible tube proximate the base of the filter; and
a mid-portion of each strut is spaced apart from and not connected to the filter.

2. A system for percutaneous retrograde endovascular filtering and embolectomy/thrombectomy according to claim 1, wherein the base of the filter is open to the flexible tube.

3. A system for percutaneous retrograde endovascular filtering and embolectomy/thrombectomy according to claim 1, wherein:
a lower section of each strut extends outwardly away from the base of the filter to the mid-portion; and
an upper section of each strut extends inwardly from the mid-portion towards a central axis of the filter when the filter device is in the deployed position.

4. A system for percutaneous retrograde endovascular filtering and embolectomy/thrombectomy according to claim 3, wherein:
the mid-portion of each strut expands to a first diameter greater than that of the constraining sleeve when the filter device is in the deployed position; and
the mid-portion of each strut is contracted to a second diameter approximate that of the constraining sleeve when the filter device is in the partially withdrawn position.

5. A system for percutaneous retrograde endovascular filtering and embolectomy/thrombectomy according to claim 1, further comprising an aspiration port positioned at a second end of the flexible tube.

6. A system for percutaneous retrograde endovascular filtering and embolectomy/thrombectomy according to claim 1, wherein the filter comprises a nitinol mesh.

7. A system for percutaneous retrograde endovascular filtering and embolectomy/thrombectomy according to claim 1, wherein the filter comprises a porous polymer matrix.

8. A system for percutaneous retrograde endovascular filtering and embolectomy/thrombectomy according to claim 1, wherein the filter comprises a synthetic or metallic mesh.

9. A system for percutaneous retrograde endovascular filtering and embolectomy/thrombectomy according to claim 1, wherein each independent strut extends longitudinally from the first end of the flexible tube towards the open end of the filter without contacting another independent strut.

10. A system for percutaneous retrograde endovascular filtering and embolectomy/thrombectomy, comprising:
a constraining sleeve;
a filter device positioned within the constraining sleeve, comprising:
a flexible tube;
a filter, comprising:
a base disposed at and open to a first end of the flexible tube; and
an expandable open end opposite the base; and
a set of deployable independent struts disposed peripherally around the filter, wherein:
each independent strut extends longitudinally from the first end of the flexible tube towards the expandable open end of the filter without contacting another independent strut;
a first end of each strut:
is coupled to the expandable open end of the filter;
expands outwardly to open the filter when the filter device is in the deployed position;
contracts to close the filter when the filter device is in the partially withdrawn position;
a second end of each strut is coupled to the flexible tube proximate the base of the filter; and
a mid-portion of each strut is spaced apart from and not connected to the filter.

11. A system for percutaneous retrograde endovascular filtering and embolectomy/thrombectomy according to claim 10, wherein:
a lower section of each strut extends outwardly away from the base of the filter to the mid-portion; and
an upper section of each strut extends inwardly from the mid-portion towards a central axis of the filter when the filter device is in the deployed position.

12. A system for percutaneous retrograde endovascular filtering and embolectomy/thrombectomy according to claim 11, wherein:
the mid-portion of each strut expands to a first diameter greater than that of the constraining sleeve when the filter device is in the deployed position; and
the mid-portion of each strut is contracted a second diameter approximate that of the constraining sleeve when the filter device is in the partially withdrawn position.

13. A system for percutaneous retrograde endovascular filtering and embolectomy/thrombectomy according to claim 10, further comprising an aspiration port positioned at a second end of the flexible tube.

14. A system for percutaneous retrograde endovascular filtering and embolectomy/thrombectomy according to claim 10, wherein the filter comprises a nitinol mesh.

15. A system for percutaneous retrograde endovascular filtering and embolectomy/thrombectomy according to claim 10, wherein the filter comprises a porous polymer matrix.

16. A system for percutaneous retrograde endovascular filtering and embolectomy/thrombectomy according to claim 10, wherein the filter comprises synthetic or metallic mesh.

* * * * *